US006833131B1

(12) United States Patent
Smith

(10) Patent No.: US 6,833,131 B1
(45) Date of Patent: Dec. 21, 2004

(54) ANTIVENOM IMMUNESERA

(75) Inventor: Damon Charles Smith, Essex (GB)

(73) Assignee: Protherics Inc., Brentwood, TN (US)

( * ) Notice: Subject to any disclaimer, the term of this patent is extended or adjusted under 35 U.S.C. 154(b) by 0 days.

(21) Appl. No.: 08/137,168

(22) PCT Filed: Apr. 24, 1992

(86) PCT No.: PCT/GB92/00761

§ 371 (c)(1), (2), (4) Date: Aug. 5, 1994

(87) PCT Pub. No.: WO92/19280

PCT Pub. Date: Nov. 12, 1992

(30) Foreign Application Priority Data

May 2, 1991 (GB) .............................................. 9109478

(51) Int. Cl.[7] ...................... A61K 39/395; A61K 35/64; C07K 16/00; G01N 33/53
(52) U.S. Cl. .................... 424/130.1; 424/542; 424/804; 424/809; 435/975; 514/829; 530/387.1; 530/389.1; 530/856; 530/866
(58) Field of Search ........................... 530/387.1, 389.1, 530/856, 866; 424/130.1, 804, 542, 809; 435/975; 514/829

(56) References Cited

U.S. PATENT DOCUMENTS

| 4,806,346 A | * | 2/1989 | Hun et al. |
| 5,053,492 A | * | 10/1991 | Rael et al. |
| 5,196,193 A | * | 3/1993 | Carroll |
| 5,340,923 A | * | 8/1994 | Carroll |

FOREIGN PATENT DOCUMENTS

WO     WO 91/00636     1/1991

OTHER PUBLICATIONS

Dos Santos et al, Toxicom 27(3): 297–303, 1989.*
Russell et al, Am. J. Trop Med. Hyg. 34(1), 1985 p. 141 Abstract.*
Own by et al, Toxicon, 28(2): 189–200, 1990.*
Campbell, Alisa M. in Laboratory Techniques in Biochemistry and Molecular Biology, 1991, by Elsevier pp. 3, Section 1.2.1.*
Goding (1983) "Monoclonal Antibodies; Principles and Practice," Academic Press, Inc., Orlando; pp. 250–261.*
"Physicians' Desk Reference" (1990) Medical Economics Company, Inc., N.J., pp. 2344–2345.*
"Stedman's medical Dictionary", 28th ed. (1990), Williams & Wilkins, Baltimore, MD., pp. 100 ad 652–653.*
Delori et al. (1996), In "Animal, Plant, and Microbiol Toxins" (A. Ohsaka et al., eds.), Plenum Press, N.Y., pp. 407–419.*
dos Santo et al. (1989) Toxicon 27(3):297–303.*
Sullivan et al. (1987) Ann. Emergency Medicine 16:938–944.*
Bailey et al (1991) Toxicon 29(6): 777–781.*
Egen et al (1994) Vet. Human Toxicol. 36(4): 362.*
Smith et al (1992) Toxicon 30(8): 865–871.*
Rawrat et al (1994) Toxicon 32(2): 185–190.*
Goding (1983) "Monoclonal Antibodies: Principles and Practice," Academic Press, Inc., Orlando, Fla., pp. 250–261.*
Berkow et al (eds.) (1987) "The Merck Mannual," Merck Sharp & Dohme Research Laboratories, Rahway, N.J., pp. 2565–2571.*
Sjostrom et al (1994) Toxicon 32(4): 427–433.*
Karlsson, E. (1979) Chemistry of protein toxins in snake venomes, In "Snake Venoms" Chapter 5, Handbook of Experimental Pharmacology No. 5, edited by C. Y. Lee. Springer–Verlag, New York.
Tu, A.T. (1982) "Rattlesnake Venoms, Their Action and Treatment." Chapter 1, Marcel Dekker Inc., New York.
Russell, F.E. (1983) Snake Venom Poisoning, Chs. 1, 6 & 7, Second Edition, Great Neck, NY.
Sewall, H. (1887) Experiments on the Preventive Inoculation of Rattlesnake Venom, *J. Physiol.*, No. 8, 203.
Sidki, A.M., et al. (1987) "Quinine Directly Determined in Serum or Urine by Separation Fluoroimmunoassay," *Clin. Chem.* 33(4), pp. 463–467.
Theakston, R.D.G., "The Application of Immunoassay Techniques, Including Elisa, to Snake Venom Research," *Toxicon.* 21(3), 352 (1983).
Laemmli, U., *Nature* 227, 680 (1970).
Chem. Abstracts, vol. 86, No. 23, Jun. 6, 1977, P. Delori et al., "Some news and comments about a rational and efficient antivenomous serotherapy," Abs. No. 166171g.
Ownby et al., *Toxicon* 28(2), pp. 189–200 (1990), Abs. No. 7470478.
Christensen, P.A., "The Preparation and Purification of Antivenoms," *Mem. Inst. Butantan Simp. Internac.* 33(1):245–250, 1966.
Kaiser et al., "Cross–Reactivity and Neutralization by Rabbit Antisera Raised Against Crotoxin, its Subunits and Two Related Toxins", *Toxicon*, vol. 24, No. 7, pp. 669–678 (1986).

* cited by examiner

*Primary Examiner*—Mark Navarro
(74) *Attorney, Agent, or Firm*—Wolf, Greenfield & Sacks, P.C.

(57) ABSTRACT

An antivenom comprising a mixture of monospecific antisera each raised against venoms of one species or subspecies is disclosed. Also disclosed is a pharmaceutical composition comprising the antivenom of the invention, and a method of treating envenomation in a mammal comprising administering the claimed antivenom.

3 Claims, 2 Drawing Sheets

ANTIVENOM IMMUNESERA

FIELD OF THE INVENTION

1. Background of the Invention

The present invention relates to antivenoms and processes for their preparation. More particularly, the invention relates to snake antivenoms and processes for their preparation.

2. Description of Related Art

A number of animals including snakes, gila monsters, spiders and bees produce venoms which are hazardous to man. For example, approximately one million people throughout the world are bitten each year by poisonous snakes. It has been estimated that of these some 100,000 die and that another 300,000 will suffer some form of disability for the remainder of their lives. This is probably a gross underestimation due to lack of detailed records from some parts of the world.

Snake venoms, produced primarily for the procurement of prey or in a defensive role, are complex biological mixtures of upwards of 50 components. Death of prey from a snake bite is due to respiratory or circulatory failure caused by various neurotoxins, cardiotoxins (also called cytotoxins), coagulation factors, and other substances acting alone or synergistically. Snake venoms also contain a number of enzymes which when injected into the prey start tissue digestion. The venoms thus contain substances designed to affect the vital processes such as nerve and muscle function, the action of the heart, circulation of the blood and the permeability of membranes. Most constituents of snake venoms are proteins, but low molecular weight compounds such as peptides, nucleotides and metal ions are also present (1).

Poisonous snakes may be divided into 4 main families,

TABLE 1.1

Classification of venomous snakes

Class: Reptilla (Reptiles)
Order: Squamata (Snakes and Lizards)
Suborder: Serpentes (Snakes)
Infra order: Alethinophidia (Spectacled Snakes)
Superfamily: Colubroidea (Advanced Snakes)

| Family | Subfamily | Tribe |
|---|---|---|
| Colubridae (Colubrid Snakes) | Nactricinae (Nactricine Water Snakes) Dispholidinae (African Rear-Fanged Snakes) Atrctaspidinae (Burrowing False Vipers) | |
| Elapidae (Palatine Erectors) | Bungarinae (Cobras) Elapinae | Bungarini (Kraits) Najini (Cobras) Elapini (American Coral) Maticorini (Asian Coral) Laticaudini (Sea Kraits) |
| Hydrophhiidae (Palatine Draggers) | Oxyuraninae (Australasian Venomous Snakes) Hydrophiinae (True Sea Snakes) | Ephalophini Hydrelapini Aipysurini Hydrophini |
| Viperidae (Vipers) | Viperinae (Pitless Vipers) | Viprini (True Vipers) Azemiopini (Fea's Viper) Causini (Night Adders) |

TABLE 1.1-continued

Classification of venomous snakes

| | Crotaline (Pit Vipers) | Lachesini (Bushmasters) Crotalini (Viviparous Pit Vipers) |
|---|---|---|

TABLE 1.2

Classification and geographical distribution of subfamily Crotalinae.

| Tribe | Genus | Habitat |
|---|---|---|
| Lachesini | Lachesis (Bushmasters) | Central and South America |
| Crotalini | Crotalus (Rattlesnakes) | North, Central and South America |
| | Sistrurus (Massaugas and pigmy rattlesnakes) | North America |
| | Bothrops (New World pit vipers) | Central and North America |
| | Trimeresurus (Asiatic pit vipers) | Asia and North America |
| | Hypnale | Asia |
| | Agkistrodon (Moccasin) | North America, Southeast Europe, and Asia | the Colubridae, the Viperidae, the Hydrophidae and the Elapidae (2). The systematics of these snakes is described in Tables 1.1 and 1.2. Rattlesnakes which are particular to the American continent are members of a subfamily of venomous snakes from the Viperidae family known as Crotalinae, genera Crotalus or Sistrusus (rattlesnakes) Bothrops, Apkistrodon and Trimerisurus. The two rattlesnake genera may be broken down still further into species and sub species. These snakes are also called the 'pit vipers' due to the presence of facial sensory heat pits, however their most prominent feature is the rattle which when present distinguishes them from all other snakes.

Each species or subspecies occupies a distinct geographical location in the North or South America. The venom of each species of rattlesnake contains components which may be common to all rattlesnakes, common to only some smaller groups or may be specific to a single species or subspecies (3).

Antivenom is the serum or partially purified antibody fraction of serum from animals that have been rendered immune to venom toxicity as a result of a regimen of injections of increasing doses of snake venom.

The scientific study of antivenom began with the work of Henry Sewell (5) in 1887 and has progressed throughout the present century. Currently, a large number and diversity of monospecific and polyspecific antivenoms are produced around the world.

SUMMARY OF THE INVENTION

DESCRIPTION OF THE PREFERRED EMBODIMENTS

Figure 1:
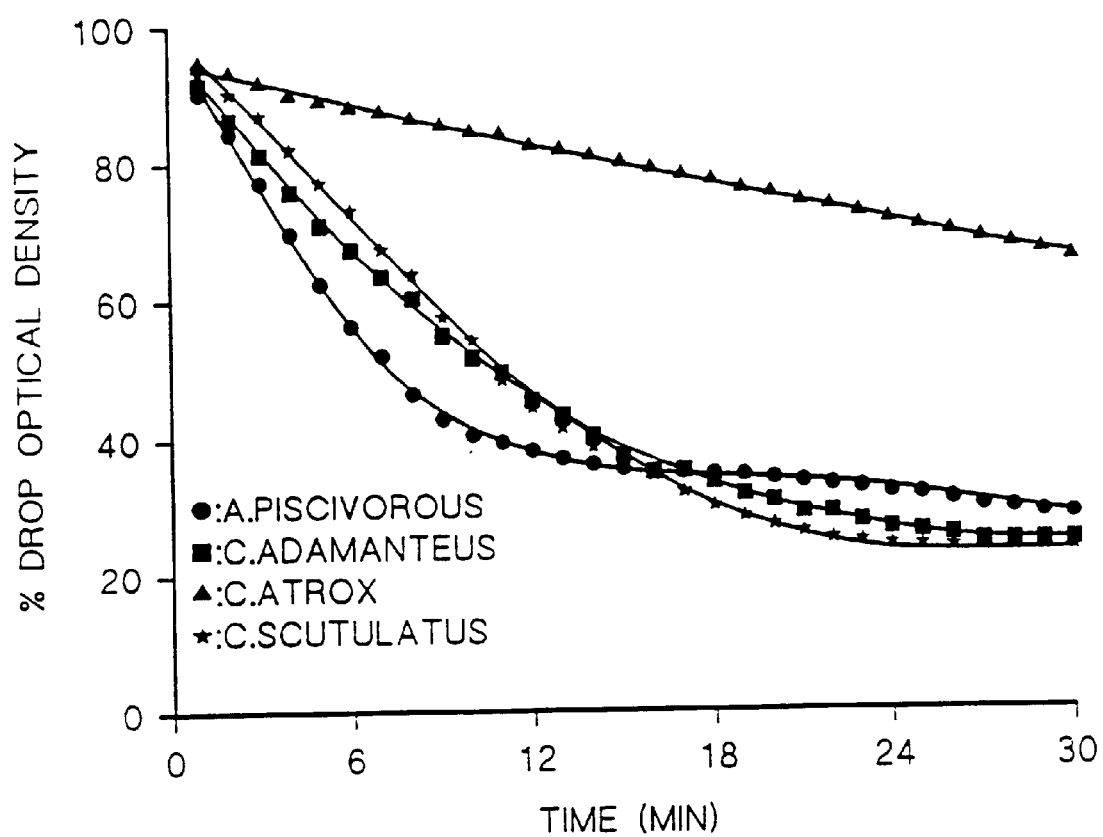
FIG. 1 illustrates the phosphate A2 activity in 1 $\mu$g of four crotalid venoms.

As used herein the term "monospecific antivenom" refers to an antivenom raised against the venom of a single species or sub-species of venomous animal. The term "polyspecific antivenom" refers to an antivenom raised against a mixture of two or more venoms from different species or sub-species of venomous animal.

The terms monospecific and polyspecific antisera are used herein in order to avoid the confusion caused by use of the common alternative expressions 'monovalent' and 'polyvalent' antisera. This terminology is used because the term "valency" is used by immunologists to express the number of binding sites possessed by an antibody or antibody digestion product, thus an IgG molecule is divalent whereas an F(ab) fragment, which has only one binding site, is monovalent. The use of the term "specificity" in describing an antiserum avoids any confusion.

In the pioneering work by Sewell, pigeons were inoculated with sublethal doses of rattlesnake venom followed by injections of increasing doses to levels above those which would, if injected initially, cause death. It was thus demonstrated that the birds had developed a resistance to the venom. In 1889, Kaufmann (6) using the European snake *Vipera berus,* obtained similar results and in 1892, Calmette (7) working in Saigon with Cobra venom reported that it was possible to confer resistance by a protocol of injections of venom. However, it was Kanthack (8) who first conferred resistance to another animal when, by mixing venom with blood from an immunised animal, he demonstrated resistance to lethal doses of the snake venom.

Calmette's basic schedule was to accustom the animal to frequent, repeated, gradually increasing doses of venom (usually cobra venom). He found that over a period of 16 months immunised horses become tolerant to 80 times the lethal dose of the venom. He also showed that the antivenom derived from blood taken from these horses had a neutralising effect of 20,000 units when applied to rabbits, that is 1 ml of serum could neutralise the minimum lethal dose of venom for 20,000 g of rabbits.

Most known antivenoms are refined concentrates of equine serum globulins prepared in a liquid or dried form. The antivenoms are obtained from horses that have been immunised against a single venom, to produce a monospecific antivenom, or a mixture of a number of venoms, to produce a polyspecific antivenom. Antivenoms have been prepared for the treatment of most types of snake venom poisoning. Methods of production have changed little since the pioneering times of the last century. Immune horse serum may undergo a crude purification step usually employing ammonium sulphate to precipitate the globulin fraction and in some cases this is the form of the final product. Since antivenoms in this form can give rise to severe serum reactions, it is known to employ pepsin digestion to remove the Fc part of the immunoglobulin which is primarily responsible for such immunogenic reactions.

The effectiveness of the known antivenoms in neutralising both the deleterious and seemingly non-deleterious effects of a specific venom may vary considerably and depends upon a number of factors. The most important of these factors are the specificity of the antivenom, the titre of the antibodies produced and the degree concentration or purification of the final product.

In general, the more specific an antivenom the greater the likelihood that it will neutralise the challenging venom. Monospecific antivenom, raised against single venoms, are therefore most effective against their homologous venom. However, such antivenoms are only of use in the treatment of a snake bite when the species or subspecies of the offending snake has been identified. When the offending snake has not been identified, as is usually the case in a "field" situation, a polyspecific antivenom, raised against a spectrum of different venoms, is preferred in order to improve the likelihood of the antivenom being effective against the venom of the unidentified snake. Conventional polyspecific antivenoms, however, lack the specifity of monospecific antivenoms and are, therefore, less effective in neutralising the pharmacological activity of a venom.

The Applicant has made the unexpected and surprising discovery that an antivenom (herein referred to as a "mixed monospecific antivenom") comprising a mixture of different antisera raised separately to different venoms is more effective in neutralising the pharmacological activity of a venom than a conventional polyspecific antivenom prepared by raising a single antiserum to a spectrum of venoms, but retains the broad specificity of polyspecific antivenoms.

According to a first aspect of the present invention there is provided an antivenom comprising a mixture of at least two different antisera raised to different venoms.

It is postulated that antivenoms comprising a mixture of different antisera are more effective than conventional polyspecific antivenoms because the former may contain a higher proportion of antibodies directed against the low molecular weight and/or poorly immunogenic components of venoms.

Snake venoms are complex multicomponent mixtures of protein, nucleotides and metal ions. These components differ in molecular weight, in their degree of antigenicity and in their concentration in the venom. When venom is injected into an animal to raise an antiserum a number of antibody populations may be produced. The concentration and affinities of the antibodies raised will vary according to various criteria, for example, the number of epitopes on the surface of a component, the immunogenicity of each epitope, the concentration of each component. The lethal, neurotoxic components of venoms (including, for example, rattlesnake venoms) often comprise low molecular weight, poorly immunogenic components present only in low concentrations. Such components are unlikely to elicit high titre antibodies.

It is postulated that this problem is exacerbated in the production of a polyspecific antivenom by using an immunising mixture comprising a mixture of venoms in which the low concentration, low molecular weight and poorly immunogenic components are further diluted by highly immunogenic components. Production of a polyspecific antivenom therefore results in an antivenom in which antibodies to some components do not exist or are in such low concentration that their effectiveness is negligible.

In contrast, the mixed monospecific antivenom of the present invention comprises a mixture of antisera raised to different venoms in separate groups of animals. By raising the antisera separately, the number of possible antibody populations that is available for each antiserum is the same but the number of epitopes in the immunogen is significantly less. Thus, it is postulated that the component antisera contain a higher proportion of protective antibodies against low molecular weight, poorly immunogenic components than polyspecific antivenoms. Combination of the monospecific antisera to produce a mixed monospecific antiserum results in an antivenom which has all the populations of the monospecific serum, and therefore conveys better protection, but also has the advantages of a polyspecific antivenom in that the cross reactivity of the antivenom has been maximised.

It will be appreciated that each component antivenom of the mixed monospecific antivenom of the present invention may itself be a monospecific antivenom or a polyspecific antivenom. For example, the mixed monospecific antivenom may comprise a mixture of a polyspecific antivenom raised to venoms A+B and a monospecific antivenom raised to venom C.

Preferably, each component antivenom is a monospecific antivenom. For example, the mixed monospecific antivenom may comprise a mixture of monospecific antivenoms raised to venoms A, B and C.

The antisera which comprise the mixed monospecific antivenom may be mixed in any suitable proportion. Preferably the mixed monospecific antivenom contains antisera mixed in a proportion appropriate to the geographical area in which the mixed monospecific antivenom is intended for use. Factors that may be taken into consideration when producing such a "bespoke" mixed monospecific antivenom are the population, distribution, behaviour and toxicity of a particular venomous animal within a particular area.

The composition of the mixed monospecific antivenom may be determined by a statistical analysis of bites on humans in a particular geographical area by particular species or sub-species of venomous animal. Preferably, each component antisera of the mixed monospecific antivenom is present in direct proportion to the relative frequency of bites on humans in a particular geographical area by the particular species or sub-species of venomous animal against whose venom the antiserum is raised.

For example, the Diamond-back rattlesnake is separated into two geographical types known as the Eastern (C.adamanteus) and the Western (C.atrox) Diamond-back. A mixed monospecific antivenom can therefore be produced which caters for the snakes of a particular geographical area. The inclusion of antisera against snakes not found in that area, which might dilute the effectiveness of any product, is therefore not necessary. This ability to produce bespoke antivenoms allows the mixed monospecific antivenoms of the present invention to approach or even to better the effectiveness of an homologous monospecific antivenom without knowledge of the offending snake by statistically compensating for the type of snake bite in a geographical region.

The antisera which comprise the antivenom may be raised in any suitable animal, for example, a mouse, rat, sheep, goat, donkey or horse. Preferably, the antisera are raised in sheep. The raising of antisera in sheep is particularly advantageous over the traditional method of raising antisera in horses as antisera raised in sheep contains none of the particularly immunogenic IgG and IgG(T) components of horse antisera which cause undesirable immunogenic serum reactions in humans or animals to whom the antivenom is administered.

The antisera which comprise the antivenom may be whole antisera. Preferably, the antisera may be partially digested to the F(ab')$_2$ or F(ab) fragments. Removal of the Fc fragment is advantageous in reducing the immunogenic reaction of the patient to the antivenom. Preparation of antibody fragments may be accomplished by conventional techniques, for example by pepsin or papain digestion (15).

The antisera which comprise the antivenom may be raised against the venom of any venomous animal, including snakes, gila monsters, spiders and bees. The antivenom may comprise antisera raised to the venom of a single type of animal, for example, antisera raised to the venom of different species or sub-species of snake. Alternatively, the antivenom may comprise antisera raised to the venom of more than type of animal. Preferably, the venom is snake venom. More preferably, the venom is rattlesnake venom.

The venom against which each antiserum is raised may comprise whole venom, partially purified venom, or one or more selected components of a venom. Preferably, the venom comprises whole venom.

According to a second aspect of the present invention there is provided a process for the preparation of an antivenom according to the first aspect of the invention comprising mixing at least two different antisera.

According to a third aspect of the present invention there is provided a pharmaceutical composition comprising an effective amount of antivenom according to the first aspect of the present invention in combination with a pharmaceutically acceptable carrier, diluent or excipient.

Preferably, the pharmaceutical composition is suitable for parenteral administration to a patient. More preferably, the pharmaceutical composition is suitable for intravenous injection.

According to a fourth aspect of the present invention there is provided a method of counteracting a venom comprising administration to a subject suffering from the effects of the venom an antivenom according to the first aspect of the present invention in an effective amount.

According to a fifth aspect of the present invention there is provided a kit for administering antivenom to a human or animal body comprising:

(a) an antivenom according to the first aspect of the present invention, and (b) means for injecting the antivenom into the body.

Figure 2:
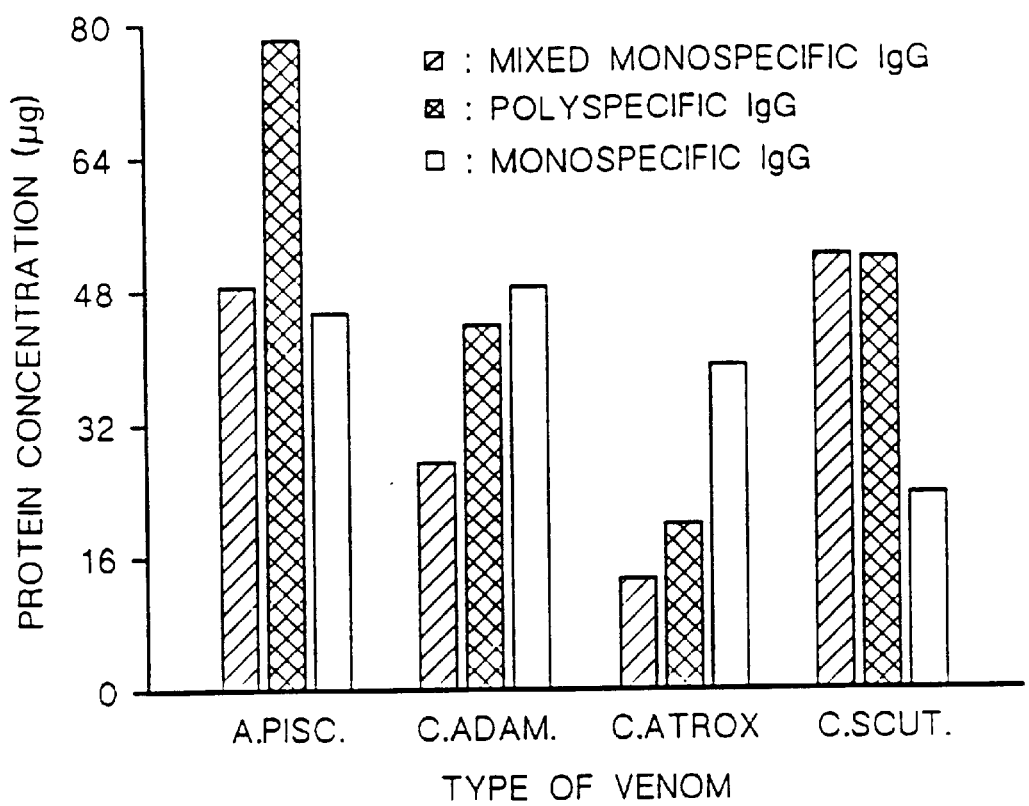
FIG. 2 illustrates the amount of antivenom needed to neutralize 50% of the phospholipase A2 activity in 1 $\mu$g of crotalid venom.

The invention will now be described by way of example with reference to the Figures in which:

FIG. 1 illustrates the phosphate A2 activity in 1 $\mu$g of four crotalid venons; and FIG. 2 illustrates the amount of antivenom needed to neutralise 50% of the phospholipase A2 activity in 1 $\mu$g of crotalid venom.

It will be appreciated that the present invention is described by way of example only and modifications of details may be made within the scope of the invention.

EXPERIMENTAL

1. Preparation of Antivenoms

An antivenom was produced by immunising a group of 10 Half-Bred Welsh ewes with a venom following the conventional immunisation schedule of Sidki et al. (11). Venom for immunisation was provided by Prof. F. Russell of Arizona University. Venom was collected from a large number of snakes of the same species. Individuals of different age and geographical location were included and venom was collected through-out the year. These factors are known to influence venom composition and are therefore important for effective production of antivenom. Blood (~300 ml) from the group is collected and pooled on a monthly basis and serum aspirated after allowing clot formation at 4° C. for 18 hours.

| WEEK | IMMUNISATION DATE | IMMUNOGEN mg/sheep | SAMPLING DATE |
|---|---|---|---|
| 0 | PRIMARY IMMUNISATION | 0.5 | |
| 1 | | | |
| 2 | | | SAMPLE 1 |
| 3 | | | |
| 4 | RE-IMMUNISATION 1 | 1.0 | |
| 5 | | | |
| 6 | | | SAMPLE 2 |
| 7 | | | |
| 8 | RE-IMMUNISATION 2 | 2.0 | |
| 9 | | | |
| 10 | | | BLEED 1 |
| 11 | | | |
| 12 | RE-IMMUNISATION 3 | 4.0 | |
| 13 | | | |
| 14 | | | BLEED 2 |
| 15 | | | |
| 16 | RE-IMNUNISATION 4 | 4.0 | |
| 17 | | | |
| 18 | | | BLEED 3 |
| 19 | | | |
| 20 | RE-IMMUNISATION 5 | 4.0 | |

An IgG concentrate is produced from the antiserum pool by sodium sulphate precipitation. The immunoglobulin fraction is then partially purified by sodium sulphate precipitation of the antiserum pool. Volumes of the antisera are mixed with equal volumes of 36% sodium sulphate and the resultant mixture is stirred for 1.5 hrs at room temperature to allow precipitation of the immunoglobulin. After centrifugation at 3500 rpm for 60 min, the pellet is washed twice with 18% sodium sulphate and the final pellet then reconstituted with phosphate buffered saline (PBS), to a volume equal to that of the initial antiserum pool. The solution is then dialysed against 20 volumes of PBS and the product is stored at 4° C. until required.

The product may be subjected to analysis by the micro-Kjeldahl method (14) to determine the exact protein concentration of the sample. If required, digestion of this IgG to form the F(ab')$_2$ and F(ab) may be performed using pepsin or papain respectively. These products may also analysed by SDS PAGE (13), micro-Kjeldahl and ELISA (12) to ensure that potency is maintained.

2. In Vitro Comparison of Antivenous 2.1 Introduction

Snake venom is a multicomponent mixture of proteins, metal ions and nucleotides. Although the exact nature of any one particular venom is particular to the genotype of the snake some common proteins exist.

One such common protein is the enzyme phospholipase A$_2$ (PLA2). This enzyme is, primarily responsible for the breakdown of body fat but may have a number of other activities such as cell rupture (via lyso products of fat hydrolysis) and neurotoxicity (mediated by a pharmacologically active site on the enzyme).

The activity of PLA2 in Crotalid or rattlesnake venoms may be assessed using a simple calorimetric assay. PLA2 hydrolyses fats to produce the fatty acid and glycerol resulting in a drop in pH of the system.

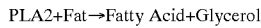

PLA2+Fat→Fatty Acid+Glycerol

This drop in pH may be monitored by the incorporation of a coloured pH indicator into the system.

2.2 PLA2 Activity Assessment

The following assay may be used to monitor the phospholipase A2 activity (PLA2, EC3.1.4) of particular venoms. Activity is assessed by measurement of free fatty acid release from a phospholipid substrate (phosphatidyl-choline, Sigma Chemical Company, product number P-9671) using a pH indicator (Cresol red, Sigma Chemical Company, product number C-9877).

Assay Buffer 1. 100 mM NaCl.
2. 100 mM KCl All GPR reagent grade.
3. 10 mM CaCl$_2$ For a routine assay 500 ml of this solution is made up and brought to pH 8.6 using a dilute sodium hydroxide solution.

Indicator Preparation 10 mg of Cresol Red (Sodium salt, Sigma No. C-9877) is dissolved in assay buffer (10 ml) and the vessel wrapped in tin foil.

Substrate Preparation

Phosphatidylcholine (1.2 g from eggyolk type XV-E, 60%, L-alpha form, Sigma No. P-9671) is dissolved in methanol (1 ml) and the solution made up to 10 ml with assay buffer (final concentration 120 mg/ml). This should be made fresh for each set of experiments.

Method

Crude freeze dried monovalent venom is dissolved in distilled water to a final concentration of 10 µg/ml. 10 ml of venom solution is routinely made up for each set of experiments. Substrate solution is then made up in the following way:

To 1 ml of the freshly prepared lipid suspension, add 25 ml of assay buffer followed by 0.3 ml of the Triton-X-100 (BDH No. 30632). Mix the solution thoroughly until it becomes clear. Adjust to pH 8.6 using dilute sodium hydroxide. Add 1 ml of the prepared indicator solution and make the substrate solution up to a final volume of 30 ml with assay buffer. (Substrate solution should be red in colour, if not the pH of the assay buffer should be checked). This solution should also be covered with silver foil.

To 2.8 ml of substrate solution in a plastic 3 ml cuvette, is added 100 µl of assay buffer and the OD$_{573nm}$ measured. 100 µl of venom solution is added and a stop-watch started. To a second cuvette containing 2.8 ml of substrate solution and 100 µl of assay buffer, a further 100 µl of assay buffer is added in order to monitor any background pH drop. This is run concurrently with the assay cuvette. Readings are taken every minute for a period of 30 minutes. A graph of OD against time is then drawn taking into account the back-ground pH drop of the control sample and subtracting this value from that caused by addition of the venom. These readings are then expressed as a percentage of the normalised control reading.

2.3 Neutralisation Studies

Neutralisation experiments are performed using IgG cuts of the relevant antisera. These preparations were obtained by salt precipitation of the whole antiserum (18% sodium sulphate, 25° C. for 1.5 h).

Assay and substrate buffers used for these studies are identical to those of the above experiments.

A 1 in 10 dilution of the antivenom in the assay buffer (stock solution) is then further diluted in doubling dilutions and 100 µl aliquots are added to 100 µl of the specific venom solution (10 µg/ml). An additional two sets of samples are made up to monitor background pH drop (200 µl assay buffer) and total hydrolysis (100 µl of assay buffer and 100 µl of venom solution). The samples are then incubated for 30 minutes at room temperature. During this period the substrate solution is made up and its pH checked.

The zero time OD of 2.8 ml aliquots of substrate solution is then measured. This is performed immediately prior to addition of 200 μl of the venom/antivenom solution (after the 30 minute incubation period). A further 15 minute incubation at room temperature is allowed and the OD then read. Results are then processed as described above, and expressed as a percentage neutralisation of the venom induced hydrolysis.

Results

The above assays were performed using four rattlesnake venoms, these being *A.piscivorøus, C.adamanteus, C.atrox* and *C.scutulatus*.

FIG. 1 demonstrates that each of the venoms contain potent PLA2 enzymes and shows the order of activity is *A.piscivorøus>C.adamanteus=C.scutulatus>C.atrox*. The PLA2 neutralising ability of the antivenoms described above was then ascertained.

Neutralisation studies were performed using a mixed monospecific antivenom made up by mixing equal volumes of equal concentration of the monospecific IgG's obtained by immunising four groups of ewes against the venom of *A.piscivorøus, C.adamanteus, C.atrox* and *C.scutulatus*. The concentrations are determined by the Kjeldahl method of Nitrogen analysis and equalised by the addition of suitable amounts of PBS.

Control neutralisation studies were also performed using monospecific antivenoms raised to each of the venoms and using polyspecific antivenom raised to a 1:1:1:1 mixture of the venoms. The control experiments used exactly analogous protocols, including venom sources, immunisation, purification and testing protocols, as the mixed monospecific antivenom experiment.

The results are illustrated in FIG. 2 which shows that the mixed monospecific antivenom is of greater or equal potency than the corresponding polyspecific antisera for neutralisation of venom PLA2 activity. Indeed, for three of the four venoms tested, significantly less antivenom was required to achieve 50% neutralisation.

In addition, the mixed monospecific antivenom was also of similar or greater potency than the homologous monospecific antivenom, showing that the mixed monospecific antivenom had a high degree of cross reactivity.

These results lead to the surprising conclusion that in the case of PLA2 neutralisation, the mixed monospecific antisera is more potent than its polyspecific counterpart.

References

1. Karlsson, E. (1979) Chemistry of protein toxins in snake venoms. In "Snake Venoms" Chapter 5, Handbook of Experimental Pharmacology No. 5 Edited by C. Y. Lee. Springer-Verlag, New York.
2. Tu, A. T. (1982) "Rattlesnake Venoms, Their Action and Treatment." Chapter 1. Marcel Dekker Inc. New York.
3. Russell, F. E. (1983) Snake Venom Poisoning. Second Edition. Great Neck. New York.
5. Sewall, H. (1887) Experiments on the Preventative Inoculation of Snake Venom. *J.Physiol.,* 8, 203.
6. Kaufman, M. (1886) *Du Venom Vipere,* Masson Paris.
7. Calmette, A. (1892) Etude Experimentale du Venin de *Naja. tripuians, Ann. Institut Pasteur.,* 6, 160.
8. Kanthack, A. A. (1897) Report on Snake Venom in its Prophylactic Relation with Poisons of the Same and Other Sorts. *Rep. Med. Local Govt. Bd.,* 1895–6, London.
9. Calmette, J. (1907) *Les Venins, Animaux et la Serotherapie Antivenimeuse,* Masson, Paris.
11. Sidki, A. M. Al Abdullah, I. H. and Rowell, F. J. (1987) Quinine Directly Determined in Serum or Urine by Separation Fluoriummunoassay. *Clin. Chem.* 33, 463.
12. Theakston, R. D. G. (1983) The Application of Immunoassay Techniques Including Elisa, to Snake Venom Research. *Toxicon.,* 21, No. 3, 352.
13. Laemmlli, U. (1970) *Nature,* 227, 680.
14. Grimble, G. K. (1990) *Clin. Lab.Practice.* 39, No. 4, 71.
15. Lamoyi E. and Nisonoff A. (1983) *J. Immunol. Meth.,* 56, 235. Porter R. R. (1959) *Biochem. J.,* 73, 119.

I claim:

1. An isolated snake antivenom comprising a mixture of four different monospecific IgG, F(ab')$_2$ fragment, or Fab fragment populations each of which is obtained from different ovine antisera, wherein each of said antisera is separately raised to a different snake venom, and wherein said snake venom is selected from a group consisting of *A. piscivorus, C. adamanteus, C. atrox,* and *C. scutulatus*.

2. A method for counteracting a snake venom comprising administering to a subject suffering from the effect of a snake venom and antivenom according to claim 1 in an effective amount.

3. A kit for administering an antivenom to a subject comprising:

(a) an isolated snake antivenom according to claim 1 and
(b) means for injecting said antivenom into the subject.

* * * * *

UNITED STATES PATENT AND TRADEMARK OFFICE
CERTIFICATE OF CORRECTION

PATENT NO. : 6,833,131 B1
DATED : February 10, 2005
INVENTOR(S) : Damon C. Smith It is certified that error appears in the above-identified patent and that said Letters Patent is hereby corrected as shown below:

Column 10,
Line 38, delete "and" and substitute therefor -- an --.

Signed and Sealed this

Twenty-sixth Day of April, 2005

JON W. DUDAS
*Director of the United States Patent and Trademark Office*